United States Patent [19]

Paciorek et al.

[11] 4,215,072
[45] Jul. 29, 1980

[54] DIPHOSPHA-S-TRIAZINES

[75] Inventors: Kazimiera J. L. Paciorek, Corona Del Mar; Reinhold H. Kratzer, Irvine; Jacquelyn Kaufman, Costa Mesa; Thomas I. Ito; James H. Nakahara, both of Fountain Valley, all of Calif.

[73] Assignee: The United States of America as represented by the Secretary of the Air Force, Washington, D.C.

[21] Appl. No.: 10,092

[22] Filed: Feb. 7, 1979

[51] Int. Cl.$^2$ .............................. C07F 9/65; C07F 9/28
[52] U.S. Cl. .............................. 260/551 P; 252/49.9; 252/400 A; 252/389 A
[58] Field of Search .................. 260/551 P; 252/49.9, 252/400 A, 389 A

[56] References Cited

U.S. PATENT DOCUMENTS

| 3,646,134 | 2/1972 | Hunger | 260/551 P |
|---|---|---|---|
| 3,882,103 | 5/1975 | Beriger et al. | 260/551 P X |
| 4,006,203 | 2/1977 | Chance et al. | 260/551 P X |

OTHER PUBLICATIONS

Appel et al., CA 78: 111439e (1973).

Primary Examiner—Thomas A. Waltz
Attorney, Agent, or Firm—Joseph E. Rusz; Cedric H. Kuhn

[57] ABSTRACT

Diphospha-s-triazines wherein the two phosphorus atoms are substituted by aromatic groups and the carbon atom is substituted by either a perfluoroalkyl or a perfluoroalkylether moiety. The triazines exhibit a broad range of properties and are useful as antioxidant-anticorrosion agents, lubricants, and hydraulic fluids.

5 Claims, No Drawings

DIPHOSPHA-S-TRIAZINES

RIGHTS OF THE GOVERNMENT

The invention described herein may be manufactured and used by or for the Government of the United States for all governmental purposes without the payment of any royalty.

FIELD OF THE INVENTION

This invention relates to diphospha-s-triazines. In one aspect it relates to a process for synthesizing the triazines.

BACKGROUND OF THE INVENTION

Because of their thermal stability, perfluorinated fluids have a great potential for use as engine oils, hydraulic fluids and greases. However, there is a serious drawback in their use, resulting from the fact that certain metals, e.g., certain ones present in aircraft engine components, are corroded by the fluids at temperatures above 550° F. in an oxidative environment. It would be highly desirable to provide an additive for the fluids that would overcome the corrosion problem associated with their use.

It is a principal object of this invention, therefore, to provide an antioxidant-anticorrosion additive for perfluorinated fluids.

Another object of the invention is to provide diphospha-s-triazines.

A further object of the invention is to provide a process for synthesizing the triazines.

Other objects and advantages of the invention will become apparent to those skilled in the art upon consideration of the accompanying disclosure.

SUMMARY OF THE INVENTION

The present invention resides in diphospha-s-triazines (triazines) having the following formula:

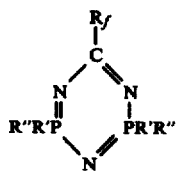

wherein $R_f$ is a perfluoroalkyl or perfluoroalkylether group, and R' and R" are the same or different aryl groups. Examples of the $R_f$ substituent include groups having the formula $C_nF_{2n+1}$, where n is an integer from 1 to 10, inclusive, $CF_3(OCF_2CF_2)_xOCF_2$, $C_2F_5—(OCF_2CF_2)_xOCF_2$, and $C_3F_7[OCF(CF_3)CF_2]_x$-$OCF(CF_3)$, where x is zero or an integer from 1 to 20, inclusive, preferably an integer from 1 to 4, inclusive. Examples of the R' and R" groups include $C_6H_5$, R—$C_6H_4$, where R is an aromatic, alkyl, perfluoroalkyl or perfluoroalkylether moiety, and a perfluoroaryl, such as $C_6F_5$ and $R_f'$—$C_6F_4$, where $R_f'$ is a perfluoroalkyl or perfluoroalkylether group.

In one embodiment, the present invention resides in a process for preparing the triazines. The procedure followed in synthesizing the triazines can be represented by the following equation:

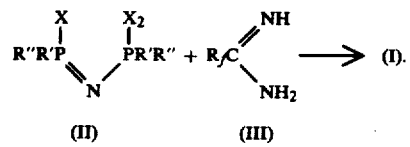

In the foregoing equation $R_f$, R' and R" are as defined above while X is chlorine or bromine. As shown by the equation, an imidotetraaryl-diphosphinic acid trihalide (II) is reacted with perfluoroalkyl or perfluoroalkylether amidine (III), giving the diphospha-s-triazine (I). During the reaction, which is conducted at a temperature ranging from about 95° to 155° C., hydrogen halide is evolved. The reaction period usually ranges from about 50 to 250 hours although longer and shorter periods can be used. The reaction is carried out under an inert gas, such as nitrogen, helium or argon. In general, equimolar amounts of the reactants are utilized although it is often preferred to employ a small excess of the diphosphinic acid trihalide (II). For example, the mole ratio of compound II to compound III can vary from about 1 to 1.5 to 1.

The materials that are used in preparing the triazine products are known compounds that are described in the literature. For example, imido-tetraphenyl-diphosphinic acid trichloride is described by E. Fluck et al in Chem. Ber., 96, 3091 (1963). Perfluoro-n-heptylamidine is described by H. C. Brown in J. Polymer Sci., 44, 9 (1960) and by D. R. Husted in U.S. Pat. No. 2,676,985 (1954). Perfluoroalkylether amidines are described by P. D. Schuman et al in British Pat. No. 1,350,806 (1974).

A more complete understanding of the invention can be obtained by referring to the following illustrative examples which are not intended, however, to be unduly limitative of the invention.

EXAMPLE I

Under nitrogen by-pass into a hot suspension of imido-tetraphenyl-diphosphinic acid trichloride (7.62 g) (15.53 mmole) in s-tetrachloroethane (110 ml) was added perfluoro-n-heptylamidine (6.01 g) (14.58 mmole) over a period of 1.5 hours. The resulting mixture was then heated at 96°-100° C. for 110 hours. Subsequently, the solvent was removed in vacuo and the residue was treated with hot heptane. The hot heptane soluble material crystallized on cooling, giving 3.68 g (32% yield) of 1,3-bis(diphenylphospha)-5-perfluoro-n-heptyl-2,4,6-triazine (mp 84.5°-85.5° C.).

Analysis Calc'd for $C_{32}H_{20}F_{15}N_3P_2$: C,48.49; H, 2.54; F,35.92; N,5.30; P,7.81. Found: C,47.74; H,2.49; F,37.27; N,4.89; P,7.89.

Molecular weight calc'd: 793.45. Found: 830.

EXAMPLE II

A mixture of imido-tetraphenyl-diphosphinic acid trichloride (5.50 g) (11.21 mmole) and perfluoroalkylether amidine, $C_3F_7OCF—(CF_3)C$-$F_2OCF(CF_3)C(=NH)NH_2$, (4.64 g) (9.40 mmole) was heated under nitrogen by-pass at 125°-130° C. for 158 hours. The residue was subsequently distilled in vacuo, giving 1,3-bis(diphenylphospha)-5-[$C_3F_7OCF(CF_3)C$-$F_2OCF(CF_3)$]-2,4,6-triazine (4.51 g) (56% yield) (bp 153°-158° C./0.001 mm Hg).

Analysis Calc'd for $C_{33}H_{20}F_{17}N_3O_2P_2$: C,45.28; H,2.30; F,36.89; N,4.80; P,7.08; O,3.66. Found: C,45.52; H,2.45; F,39.66; N,4.30; P,6.95.

Molecular weight calc'd: 875.46. Found: 895.

EXAMPLE III

A mixture of imido-tetraphenyl-diphosphinic acid trichloride (5.94 g) (12.10 mmole) and perfluoroalkylether amidine, $C_3F_7O[CF-(CF_3)CF_2O]_2CF(CF_3)C(=NH)NH_2$, (7.64 g) (11.57 mmole) was heated under nitrogen by-pass at 120°–156° C. for 10 days. The residue was thereafter filtered through a 1.8×20 cm column of basic alumina and then distilled in vacuo, giving 7.80 g (65% yield) of 1,3-bis(diphenylphospha)-5-[$C_3F_7O[CF(CF_3)CF_2O]_2CF(CF_3)$]-2,4,6-triazine (bp 167°–170° C./0.001 mm Hg).

Analysis Calc'd for $C_{36}H_{20}F_{23}N_3O_3P_2$: C,41.52; H,1.94; F,41.96; N,4.03; P,5.95; O,4.61. Found: C,41.30; H,2.21; F,43.88; N,3.71; P,5.25.

Molecular weight calc'd: 1041.48. Found: 1130.

The above diphospha-s-triazine exhibited high thermal and thermal oxidative stability as evidenced by the recovery of 98 and 99% of the unchanged starting material after 24 hour heat treatment at 316° C. in nitrogen and 24 hours at 235° C. in air, respectively.

Incorporation of the diphospha-s-triazines of this invention in perfluoroalkylether fluids, e.g., fluids of the type disclosed in U.S. Pat. No. 3,393,151, inhibits the oxidation-corrosion of various metals with which the fluids come into contact. In general, only small amounts of the additives are required, e.g., about 0.05 to 5.0 percent by weight of the base fluid. In addition to being useful as antioxidants and anticorrosion agents, the diphospha-s-triazines provide candidates for high temperature lubricants and hydraulic fluids.

As will be evident to those skilled in the art, modifications of the present invention can be made in view of the foregoing disclosure without departing from the spirit and scope of the invention.

We claim:

1. A diphospha-s-triazine having the following structural formula:

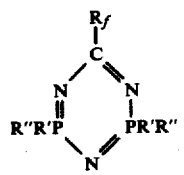

where $R_f$ is a perfluoroalkyl or perfluoroalkylether group, and R' and R" are each the same or different aryl group.

2. The triazine according to claim 1 in which $R_f$ is a group having the formula $C_nF_{2n+1}$, where n is an integer from 1 to 10, inclusive, $CF_3(OCF_2CF_2)_xOCF_2$, $C_2F_5(OCF_2CF_2)_xOCF_2$, or $C_3F_7[OCF(CF_3)-CF_2]_xOCF(CF_3)$, where x is zero or an integer from 1 to 20, inclusive; and R' and R" are individually selected from the group consisting of $C_6H_5$, $R-C_6H_4$, where R is an aromatic, alkyl, perfluoroalkyl or perfluoroalkylether moiety, $C_6F_5$ and $R_f'-C_6F_4$, where $R_f'$ is a perfluoroalkyl or perfluoroalkylether moiety.

3. The triazine according to claim 2 in which $R_f$ is $C_7F_{15}$ and R' and R" are each $C_6H_5$.

4. The triazine according to claim 2 in which $R_f$ is $CF(CF_3)OCF_2CF(CF_3)OC_3F_7$ and R' and R" are each $C_6H_5$.

5. The triazine according to claim 2 in which $R_f$ is $CF(CF_3)[OCF_2CF(CF_3)]_2OC_3F_7$ and R' and R" are each $C_6H_5$.

* * * * *